United States Patent [19]

Anderson

[11] 4,007,531

[45] Feb. 15, 1977

[54] DUAL DENTURE MODEL SURVEYOR

[76] Inventor: Earl L. Anderson, P.O. Box 1601, Grand Rapids, Mich. 49501

[22] Filed: May 22, 1975

[21] Appl. No.: 579,932

[52] U.S. Cl. .................................................. 32/67
[51] Int. Cl.² .......................................... A61C 3/00
[58] Field of Search ................................. 32/67, 32

[56] References Cited

UNITED STATES PATENTS

| | | | |
|---|---|---|---|
| 2,621,407 | 12/1952 | Schlesinger | 32/32 |
| 3,417,471 | 12/1968 | Mitchell | 32/67 |

*Primary Examiner*—Robert Peshock
*Attorney, Agent, or Firm*—Willis Bugbee

[57] ABSTRACT

A base plate carries a denture model surveyor table having model clamping fingers and a clamping screw; also a column to which is pivoted, by a ball joint, a universally-adjustable surveyor tool head including an inclined shaft horizontally pivoted to a horizontal shaft. Rotatably mounted on the forward end of this shaft is a stub shaft carrying a horizontal transverse bearing rotatably supporting the hub of a double-disc reel. Secured to the outer sides of the reel discs are two parallel chordal slide bars upon each of which is slidably mounted a chordal slider from which an axial slide bar projects perpendicularly outward. Slidably mounted on each axial slide bar is an axial slider. Depending from and tiltable relatively to each axial slider is an elongated telescoping tubular tool holder terminating in a tool chuck.

7 Claims, 3 Drawing Figures

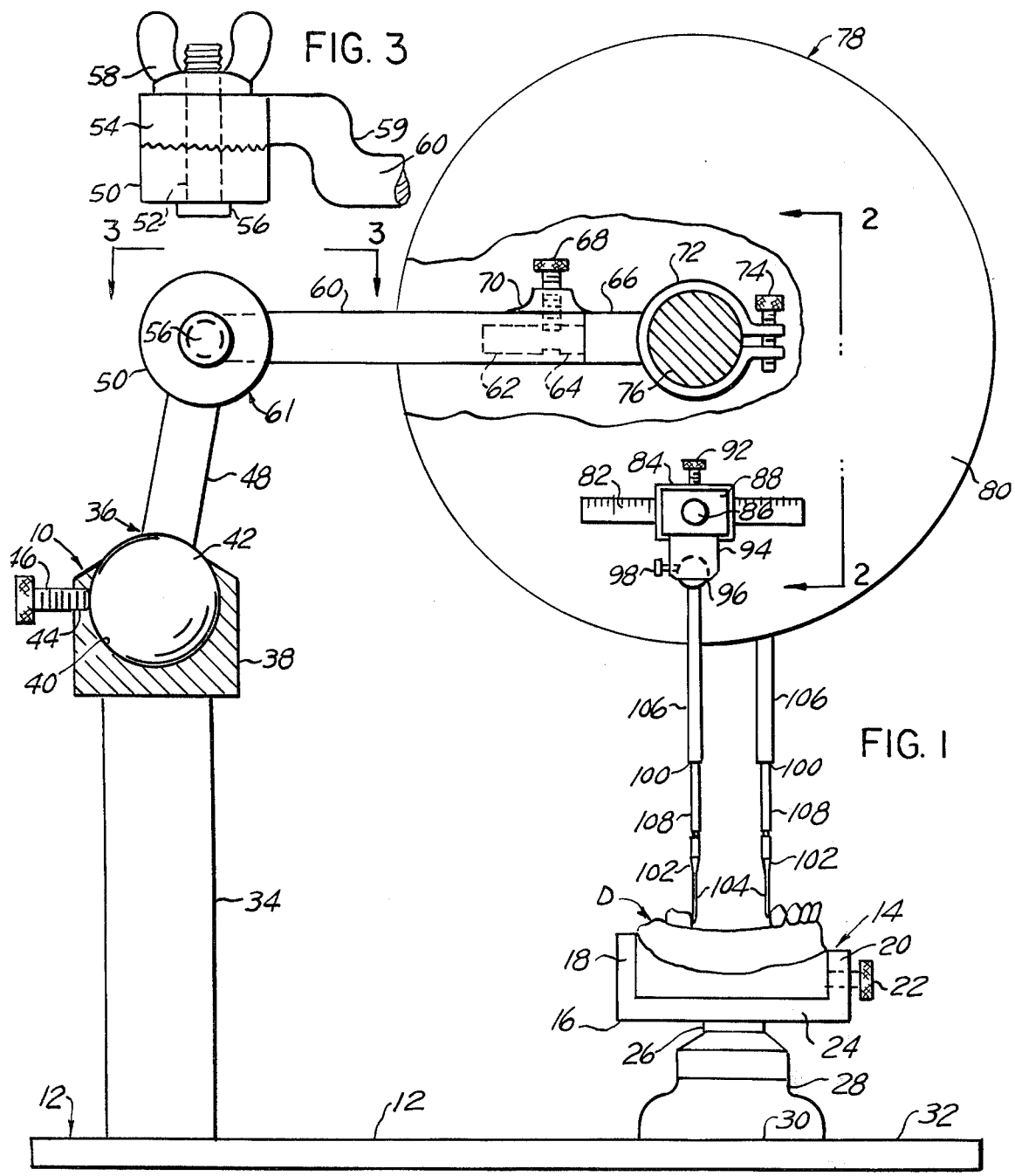
FIG. 3
FIG. 1
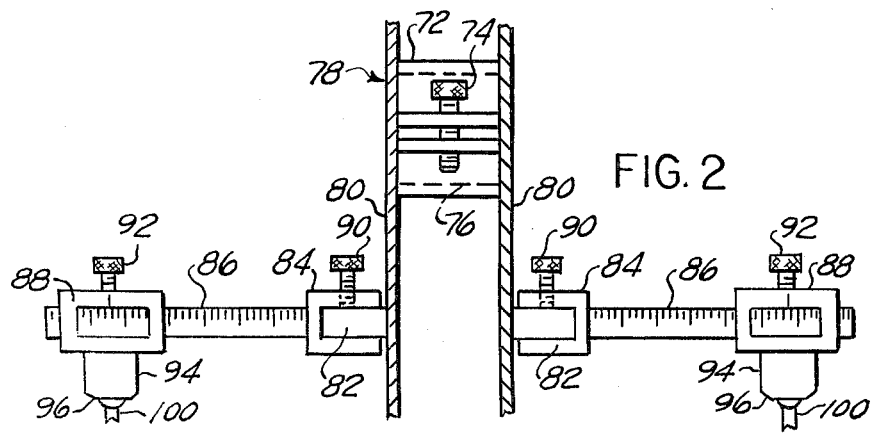
FIG. 2

DUAL DENTURE MODEL SURVEYOR

SUMMARY OF THE INVENTION

The invention particularly resides in all adjustments of the surveyor tools being made overhead in the surveyor tool head, with the denture model fixedly clamped in a stationary horizontal position during operation. The multiple adjustment devices in the tool head enable the dual tools or markers held in the two chucks to be variously positioned relatively to the denture model held in a stationary horizontal position in the surveyor table, the dual tools being located on opposite sides of the denture model adjacent the inner edges thereof. The operator manipulates the tools or markers by grasping the chucks between his fingers and moves them manually in the desired directions and paths.

In the drawing,

FIG. 1 is a left-hand side elevation of the dual denture model surveyor, according to one form of the invention, with the left-hand disc of the reel broken away to disclose the construction behind it;

FIG. 2 is a fragmentary vertical section, partly in front elevation, taken along the line 2—2 in FIG. 1; and FIG. 3 is a fragmentary top plan view taken along the line 3—3 in FIG. 1.

Referring to the drawing in detail, FIG. 1 shows a dual denture model surveyor, generally designated 10, according to a preferred form of the invention, as including a base plate 12 upon which is mounted a non-tiltable denture survey table 14 in which a denture model or cast D to be worked upon is clamped in a holder 16 between laterally-spaced twin fingers 18 and a single finger 20, the latter being drilled and threaded to receive a clamping screw 22. The supporting portion 24 of the twin fingers 18 and the single finger 20 is mounted upon a pillar 26 which rises from a base 28 having a flat bottom surface 30 mounted upon the correspondingly flat upper surface 32 of the base plate 12. The twin fingers 18 and the single finger 20 are preferably disposed in a triangular arrangement.

Spaced rearwardly away from the denture model survey table 14 and rising from the top surface 32 of the base plate 12 is an upright structure or column 34 on the upper end of which is mounted a universally adjustable tool head, generally designated 36, pivoted thereto by means of a block 38 containing a spherical socket 40 tiltably receiving a ball 42. The block 38 is drilled and threaded at 44 to receive a thumb screw 46 by which the ball 42 is held in its desired position of adjustment. Secured to and rising from the ball 42 on the upper side thereof is an inclined shaft 48 on the upper end of which is mounted a circularly-ratchet-faced boss 50 having a horizontal pivot bore 52 therethrough and adjustably engaging a similar ratchet-faced coaxially-bored boss 54 held together by a common pivot bolt 56 carrying a clamping wing nut 58. Extending horizontally forward from the boss 54 through an unfolded Z-shaped rearward end portion 59 is a horizontal shaft 60, which with the inclined shaft 48 and their pivotal connection 50 to 58 constitutes an elongated extensible support or elbow arm, generally designated 61. The forward end of the shaft 60 terminates in a longitudinal bore or socket 62 which telescopingly receives the reduced diameter annularly-grooved portion 64 of a stub shaft 66 which is clamped in its adjusted position by a thumb screw 68 threaded through a boss 70 on the shaft 60.

The stub shaft 66 terminates at its forward end in an annular split bearing yoke 72 which is clamped by a socket-head Allen clamping screw 74 around the hub 76 of a double disc reel or tool head 78 resembling a motion picture film reel. Secured to the outer surfaces of the discs 80 of the reel 78 and disposed as chords thereof are two parallel chordal or longitudinal slide bars 82 upon which chordal sliders 84 are slidably mounted. Secured to and projecting outward in opposite directions from the chordal or longitudinal sliders 84 and perpendicular to the chordal slide bars 82 (FIG. 2) are axial slide bars upon which lateral sliders 88 are slidably mounted. The sliders 84 and 88 are clamped in position upon their respective slide bars 82 and 86 by clamping screws 90 and 92 respectively. Projecting downward from the lateral sliders 88 are bosses 94 containing ball and socket joints 96 clamped by clamping screws 98. Mounted in each ball of each ball-and-socket joint 96 is a telescoping tube assembly 100, the lower end of which is provided with a chuck 102 in which various conventional surveyor tools 104 are removably and interchangeably mounted. One such tool is a cutting blade with a sharp edge which is manipulated by the fingers of the operator to cut away portions of the denture cast or wax. Another such tool is a carbon rod like a pencil lead which is used to manually draw lines around the patient's teeth which are to be gripped on their undercut portions by the metal prongs of the denture. Each telescoping tube assembly 100 includes a fixed upper outer tube 106 and a slidable inner tube 108.

In practice, the height of the dual denture model surveyor 10 is preferably made to correspond to the height of an average human skull with the denture model or cast D in the position which it would normally occupy in the skull, thus locating the surveyor table 14 at approximately the position of the mouth in the skull. The measurements taken by means of the millimeter scales thus correspond to those which would be taken in the skull itself.

In use, the cast made from the impression of the patient's mouth is placed on the upper side of the table 14 and clamped. The operator then adjusts the tool-holding head 36 by means of the various adjustment members 42, 50, 72, 84, 88 and 96, so that the tools 104 which he has inserted in the chucks 102 are suitably located on opposite sides of the dental cast on the inner edges thereof. The operator then grasps the chucks 102 between his fingers and manipulates them so as to move the tool 104 in the desired direction and paths.

The use of the present invention enables the denture model or cast D to be maintained in the same horizontal position that it would normally occupy in the mouth of the patient, while the survey table 14 is located at a position corresponding to that of the mouth in his skull. All adjustments of the markers or tools 104 relatively to it are made by repositioning the instrument head 36 by means of the various joints and sliders described above, thereby stabilizing the position of the survey table 14 and denture model clamped thereon. The sliders 84 and 88 and their respective slide bars 82 and 86 allow for measurements and adaptation of the tools or markers 104 to different sized casts corresponding to different sized mouths. The divided millimeter scales thereon enable the above-mentioned measurements to be measured and recorded. The telescoping tool holder 100 enables the chucks 102 and tools 104 to move upward or downward freely to permit free motion of the finger of the operator in manipulating the tools 104.

One result of the use of this surveyor is to facilitate the accurate making of partial dentures and of fitting them to the particular patient's mouth by indicating to the operator the exact location where the clips or clasps are to be placed in order to fit and hold the partial denture to the natural teeth still remaining in the mouth of the patient.

I claim:
1. A dual denture model surveyor, comprising
a base,
a denture model table mounted on said base and having means thereon for holding a denture model in a substantially horizontal position,
an upright structure mounted on said base in spaced relationship to said table,
an elongated extensible support extending forward from said upright structure and having a rearward end portion connected to said upright structure and having a forward end portion with a transverse pivotal connection thereon movable toward and away from said table,
and a dual tool head tiltably mounted on said forward end portion at said pivotal connection,
said tool head having thereon a pair of longitudinal slideways disposed in planes substantially parallel to said extensible support in laterally spaced relationship, and also having a pair of longitudinal sliders movable back and forth along said longitudinal slideways,
said tool head having a pair of oppositely-extending lateral slideways disposed perpendicularly to said longitudinal slideways and connected to and movable unitarily with said longitudinal sliders and also having a pair of lateral sliders movable to and fro along said lateral slideways,
said tool head having a surveyor tool holder mounted on and depending from each lateral slider in laterally-spaced relationship to one another.

2. A dual denture model surveyor, according to claim 1, wherein said extensible support comprises a jointed elbow arm which includes a rearward member having a first pivotal connection with said upright structure and also includes a forward member having a second pivotal connection with said rearward member.

3. A dual denture model surveyor, according to claim 1, wherein said elongated extensible support has a longitudinal axis, and wherein said tool head has a pivotal connection portion engageable therewith and coaxial with said longitudinal axis effecting rotation of said tool head around said longitudinal axis and relatively to said extensible support.

4. A dual denture model surveyor, according to claim 1, wherein said longitudinal slideways are disposed below said transverse pivot in spaced relationship.

5. A dual denture model surveyor, according to claim 1, wherein said tool head has a hub rotatably mounted on said transverse pivot and has a pair of discs mounted on said hub at opposite ends thereof, and wherein said longitudinal slideways are mounted on said discs in chordal positions thereon.

6. A dual denture model surveyor, according to claim 5, wherein said transverse pivot on said forward end of said extensible support comprises a bearing sleeve and wherein said hub is tiltably mounted in said bearing sleeve.

7. A dual denture model surveyor, according to claim 1, wherein said tool holder includes an upper tube connected to and depending from said its respective lateral slider, and also includes a lower tube telescopingly and extensibly engaging said upper tube, and further includes a tool chuck mounted on said lower tube.

* * * * *